United States Patent [19]

Stärk et al.

[11] 4,219,645

[45] Aug. 26, 1980

[54] STABILIZED NICOTINAMIDE-ADENINE DINUCLEOTIDES AND PROCESS FOR THEIR PREPARATION

[75] Inventors: Joseph Stärk; Reinhard Müller-Matthesius, both of Marburg an der Lahn, Fed. Rep. of Germany

[73] Assignee: Behringwerke Aktiengesellschaft, Marburg an der Lahn, Fed. Rep. of Germany

[21] Appl. No.: 25,052

[22] Filed: Mar. 29, 1979

[30] Foreign Application Priority Data

Apr. 1, 1978 [DE] Fed. Rep. of Germany ....... 2814154

[51] Int. Cl.$^2$ ...................... C07H 17/00; C07H 15/12
[52] U.S. Cl. ........................................ 536/27; 536/28; 536/29
[58] Field of Search .............................. 536/28, 27, 26

[56] References Cited

U.S. PATENT DOCUMENTS

| 3,776,900 | 12/1973 | Hammer | 536/28 |
|---|---|---|---|
| 3,819,487 | 6/1974 | Bernt et al. | 536/27 |

FOREIGN PATENT DOCUMENTS

| 46-8717 | 5/1971 | Japan. |
| 1283340 | 7/1972 | United Kingdom. |

OTHER PUBLICATIONS

Chemical Abstracts, vol. 88, 1978 (148205h).

*Primary Examiner*—Johnnie R. Brown
*Assistant Examiner*—Blondel Hazel
*Attorney, Agent, or Firm*—Curtis, Morris & Safford

[57] ABSTRACT

Nicotinamide-adenine dinucleotide or the phosphate thereof, each in the reduced as well as the oxidized forms, are stabilized against activity losses in storage by the addition of hydrolytically decomposed, optionally cross-linked collagen.

9 Claims, No Drawings

STABILIZED NICOTINAMIDE-ADENINE DINUCLEOTIDES AND PROCESS FOR THEIR PREPARATION

The invention relates to stabilized nicotinamide-adenine dinucleotides, especially free nicotinamide-adenine dinuleotide in the reduced or oxidized form and the phosphate thereof, also in the reduced or oxidized form.

In clinical chemistry, biochemistry, food chemistry, pharmacology and other fields, enzymatic reactions are frequently used for analytical purposes. Especially in clinical-chemical routine diagnostics, metabolites and enzymes are frequently subjected to enzymatic tests in blood, serum, plasma, liquor and urine samples. Due to the instability of many components of the reaction it has become common practice, especially in the clinical-chemical routine laboratories, to use industrially-prepared combination packages which allow the preparation of ready-to-use reagent solutions with minimum expenditure.

It has therefore been the subject of the invention to produce compositions having the longest possible period of utilization. With view to an easy handling of the reagents, it is desirable or necessary to fill as many substances as possible of those which are required for the test performance into a single container. However, it has become evident that different substances may show a mutual adverse influence on their respective stability, even if they are present in a lyophilized or dry form. It is therefore of great importance to find appropriate additives (stabilizers) which prolong the period of utilization of the reagents.

Particularly unstable biochemical agents, which present great problems already by themselves, not only in the dissolved form, but also in the lyophilized or dry state, are nicotinamide-adenine dinucleotide and/or nicotinamide-adenine-dinucleotide phosphate, both in their reduced as well as their oxidized forms. These substances are necessary as coenzymes in a great number of enzymatic tests and in their reduced form they also represent the colorant for photometric measurement.

As a consequence of the decomposition of the abovementioned coenzymes, the substance to be detected can no longer be determined by photometry in an unobjectionable manner, or not at all, because the absorbing matter is present in a concentration that is too low, or the speed of the reaction to be measured is too low due to the reduced concentration of the coenzyme. In the case of the determination of the activity of the lactate dehydrogenase (LDH) according to the reaction scheme pyruvate−NADH$_2$ 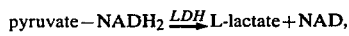 L-lactate+NAD, another complication is to be seen in the fact that the reduced coenzyme nicotinamide-adenine dinucleotide (NADH$_2$) forms LDH inhibitors in the course of storage, which inhibitors may lead to considerably false negative LDH values. Said inhibitors can already become active to a high degree before a decrease of NADH$_2$ concentration is detectable at all.

However, also in many other important determination processes, such as the detection of aspartate transaminase, alanine transaminase, α-hydroxybutyrate dehydrogenase, creatine kinase, glutamate dehydrogenase, in the fully enzymatic urea determination, the enzymatic triglyceride determination or the glucose determination according to the hexokinase process, nicotinamide-adenine dinucleotide and/or nicotinamide-adenine-dinucleotide phosphate in the reduced and/or oxidized forms belong to the sensitive components which limit the period of utilization of the test package and whose stabilization is of great interest.

In German Patent Nos. 12 89 668 and 15 98 157, glutathione as well as cysteine, cysteine carbamide and acetyl cysteine have been described as stabilizing agents for reduced nicotinamide-adenine dinucleotides. In German Patent No. 19 30 059, polyvinylpyrrolidone (PVP) has been described as stabilizer for reduced and oxidized nicotinamide-adenine-dinucleotide phosphates.

Other substances which are considered appropriate for this purpose are acacia and/or gum arabic and mannitol.

Albumin and gelatin have also been added as fillers to stabilized coenzymes (German Patent No. 19 30 059).

A process for the stabilization of biologically active material such as bacteria, bacterial metabolites, viruses, sera and enzymes has been described in German Patent No. 11 83 629. For the said purpose, use is made of a hydrolytically-decomposed gelatin, cross-linked with a diisocyanate, preferably in combination with sodium-L-glutaminate. As is shown in particular by the examples in said Patent Specification, a stabilizing agent of this kind is of importance especially for the preparation of vaccines and for the production of antigenic and immunogenic structures.

The great number of stabilizers employed shows that their activity with regard to nucleotides is not yet satisfactory.

Surprisingly, it has now been found that oxidized and reduced nicotinamide-adenine dinucleotides and also the phosphates thereof show a higher stability in reagents known so far, if they contain a hydrolytically-decomposed and optionally cross-linked collagen, preferably gelatin which has been treated in this manner.

The subject of the invention is, therefore, a stable mixture of
  (b) nicotinamide-adenine dinucleotide in the reduced or oxidized form or nicotinamide-adenine-dinucleotide phosphate in the reduced or oxidized form and
  (b) hydrolytically decomposed, optionally cross-linked collagen.

Another subject of the invention is a process for the stabilization of nicotinamide-adenine dinucleotide in the reduced or oxidized form and/or of nicotinamide-adenine-dinucleotide phosphate in the reduced or oxidized form, which comprises adding a hydrolytically-decomposed, optionally cross-linked collagen to the solution of the nucleotide, whereupon, if desired, the mixture is dried, preferably lyophilized.

The concentration of the collagen product in the aqueous solution as well as in the dry product is in the range from 0.001 to 1200 g, preferably from 0.01 to 300 g, especially from 0.5 to 20 g, for 1 g of necleotide.

Particularly appropriate collagen products are those which have been described in German Patent Nos. 11 18 792 and 11 55 134. They are prepared by decomposing collagen or its decomposition products in an aqueous solution at a temperature from 60° to 150° C. to a molecular weight of from 2000 to 20,000, preferably from 5000 to 10,000, reacting the decomposed collagen with a diisocyanate at a temperature from 0° to 100° C.

in the neutral to slightly alkaline pH range, optionally in the presence of inert organic solvents, in a manner such that the amount of isocyanate employed is smaller than that which is calculated from the number of amino and guanidino groups present in the decomposed collagen, and is preferably from about 20 to 80% of this amount, and by subsequently adjusting the cross-linked product obtained to a pH value of about 7. For cross-linking, the collagen decomposition products can also be reacted with a diisocyanate at a temperature from 0° to 100° C. in the neutral to slightly alkaline pH range, optionally in the presence of an inert organic solvent, the amount of isocyanate used being in the range from 20 to 80% of the amount calculated from the number of amino and guanidino groups present. The cross-linked product obtained is then decomposed in an aqueous solution at a temperature from 60° to 150° C. to a molecular weight of from 10,000 to 100,000 and the solution obtained is adjusted to a pH value of 7. As a solution of 3.5% strength with an average molecular weight of 35,000, the said products are also sold as infusion solutions for plasma substitution.

Although the pH value of the stabilized nucleotide solution is not of decisive importance for the stabilizing effect, it is recommended to avoid extreme pH values in view of the sensitive substances. The preferred pH range the solution is therefore in the range of from pH 5 to 11. Particularly favorable stabilizing effects have been observed at a pH value in the range of from 7 to 9.

For adjusting the pH value, the common buffer substances may be used. Examples for suitable buffer substances are mixtures various alkali metal salts of acids of low or medium strength, such as phosphoric acid or boric acid, mixtures of acids of low or medium strength with the alkali metal salts thereof (for example phthalic acid, alkali metal phthalate) or buffers comprising certain organic compounds, such as tris-hydroxymethylaminomethane or the like, as they are generally used in biochemical reactions.

The agent which has been stabilized according to the above process exhibits its excellent stability especially in a dried, preferably lyophilized, form. The weight ratio of the collagen product to nucleotide in the dry product corresponds to that of the aqueous solution.

Another subject of the invention is the use of a hydrolytically-decomposed, optionally cross-linked collagen for the stabilization of nicotinamide-adenine dinucleotide and/or nicotinamide-adenine-dinucleotide phosphate, in both cases in the reduced and the oxidized forms.

The dry nicotinamide-adenine dinucleotides stabilized in accordance with the invention and/or the mixtures thereof with the collagen product are easily soluble in water. The stabilizer of the invention shows a very low autoextinction at wavelengths of 334 nm, 366 nm or 340 nm, so that it does not produce an adverse effect in photometric measurement by an increase of the background extinction. It does not show any influence on the activity of the enzymes which are commonly used as reagents or which are to be detected, for example alanine transaminase, aspartate transaminase, lactate dehydrogenase, glutamate dehydrogenase, malate dehydrogenase or urease.

The nicotinamide-adenine dinucleotides stabilized according to the invention may be lyophilized either by themselves or together with other components which are required for the test performance. Examples for components of this kind are substrates (for example alanine, aspartate, glutamate, pyruvate, 2-oxobutyrate, 2-oxoglutarate), auxiliary enzymes (for example malate dehydrogenase, lactate dehydrogenase, urease, glutamate dehydrogenase), other coenzymes such as adenosine diphosphate or adenosine triphosphate, or buffer substances that are common in enzymology, such as trishydroxymethylaminomethane-HCl and others as specified above.

The particularly favorable stabilizing effect of the agent of the invention on nicotinamide-adenine dinucleotides may be seen from the following Examples. In this connection it is to be stated that the stability tests are carried out under a drastic temperature strain at +37° C., so that the stabilizing effect becomes evident even sooner. However, the compositions are normally stored at a temperature of from +2° to +6° C., which results in considerably higher stability values.

The following Examples serve to illustrate the invention.

EXAMPLE 1

1.14 Millimols per liter of reduced nicotinamide-adenine dinucleotide (NADH$_2$) were dissolved each in solutions with 1.56% of the stabilizer obtained according to German Patent No. 11 18 792 or with 2.1% of polyvinylpyrrolidone (PVP). The resulting mixtures were filled in equal portions into glass bottles and were lyophilized. The glass bottles were stored at +37° C. At different points of time, samples of the lyophilized product were employed for the determination of the lactate dehydrogenase (LDH) and/or the amount of NADH$_2$ remaining in the lyophilized product was detected.

The determination of the LDH activity was effected in accordance with the recommendations given by the Deutsche Gesellschaft für Klinische Chemie (German Society for Clinical Chemistry), Z.Klin.Chem.Klin.Biochem. 10, 182 (1972).

Any inhibitors formed in the storage of the lyophilized product would have become evident in the determination of the LDH activity by a reduction of the values.

The amount of NADH$_2$ remaining in the lyophilized product was determined according to W. Gerhardt et al., Scand. J.Clin.Lab.Invest. 33, 1 (1974).

| Storage at +37° C. | LDH activity with | | Amount of NADH$_2$ with | |
|---|---|---|---|---|
| | stabilizer of the invention | PVP as stabilizer | stabilizer of the invention | PVP as stabilizer |
| initial value | 100% | 100% | 100% | 100% |
| 3 days | 98% | 88% | 100% | 94% |
| 7 days | 100% | 81% | 100% | 95% |
| 14 days | 96% | 65% | 100% | 89% |
| 21 days | 100% | 56% | 98% | 82% |
| 28 days | 100% | 45% | 99% | 72% |

EXAMPLE 2

(Urea reagent)

A solution of 40 g/l of the agent obtained according to German Patent No. 11 55 134, 4.54 mmols/l of NADH$_2$, 357 mmols/l of 2-oxoglutarate and 18 U/ml of glutamate dehydrogenase (GlDH) was lyophilized in glass bottles. The glass bottles were stored at +37° C.

At determined points of time which have been shown in the Table, samples of the lyophilized product were dissolved in a tris buffer of a pH value of 8.0, thereafter an excess amount of ammonium ions was added, and the mixture was subjected to a determination of the NADH$_2$ content by way of photometry at 340 nm. The result has been given in the following Table:

| Storage at 37° C. | NADH$_2$ concentration |
|---|---|
| Initial value | 100% |
| 14 days | 93% |
| 28 days | 91% |
| 54 days | 88% |
| 84 days | 87% |

Other nucleotide-containing reagents may be stabilized in the same manner. Similarly favorable results are obtained if from 2 to 20 g of collagen product are added to 1 to 3 g of nucleotide.

EXAMPLE 3

0.86 Gram of the stabilizer obtained according to German Patent No. 11 18 792 and/or 0.86 g of polyvinylpyrrolidone (PVP) were dissolved in 55 ml of water each. Thereafter 54.6 mg of reduced nicotinamide-adenine-dinucleotide phosphate (NADPH$_2$) were dissolved each in the two liquids, the resulting mixtures were filled into glass bottles in equal portions and were lyophilized. The glass bottles were stored at +37° C. At determined points of time, which have been shown in the Table, the bottles were opened, and the NADPH$_2$ content of the lyophilized contents was measured photometrically by way of the reaction 2-oxoglutarate+NADPH$_2$+NH$_4^{(+)}$  glutamate+NADP Results:

| Storage at +37° C. | Content of NADPH$_2$ | |
|---|---|---|
| | stabilizer of the invention | PVP as stabilizer |
| initial value | 100% | 100% |
| 7 days | 100% | 98% |
| 15 days | 98% | 93% |
| 21 days | 97% | 90% |
| 28 days | 94% | 80% |

What is claimed is:
1. A stable mixture comprising
   (1) a member selected from the group consisting of oxidized nicotinamide-adenine dinucleotide, reduced nictonamide-adenine dinucleotide, oxidized nicotinamide-adenine dinucleotide phosphate, and reduced nicotinamide-adenine dinucleotide phosphate and
   (2) decomposed collagen having a molecular weight from 2000 to 20000.
2. A stable mixture as in claim 1 wherein said decomposed collagen has been cross-linked by prior reaction with a diisocyanate.
3. A stable mixture as in claim 2 wherein said decomposed collagen has been cross-linked by prior reaction with an amount of diisocyanate which is from 20 to 80 percent of the theoretical amount required for reaction with amino groups and guanidino groups present in the decomposed collagen.
4. A stable mixture as in claim 1 wherein the ratio by weight of nucleotide to decomposed collagen is between 1:0.001 and 1:1200.
5. A stable mixture as in claim 1 which is lyophilized.
6. A method for stabilizing a solution of a member selected from the group consisting of oxidized nicotinamide-adenine dinucleotide, reduced nicotinamide-adenine dinucleotide, oxidized nicotinamide-adenine dinucleotide phosphate, and reduced nicotinamide-adenine dinucleotide phosphate, which method comprises combining a solution of said member with decomposed collagen having a molecular weight from 2000 to 20,000.
7. A method as in claim 6 wherein said decomposed collagen has been cross-linked by prior reaction with a diisocyanate.
8. A method as in claim 6 wherein the stabilized solution is then lyophilized.
9. A method as in claim 7 wherein the stabilized solution is then lyophilized.

* * * * *